United States Patent
Nilsen et al.

(10) Patent No.: US 10,214,751 B2
(45) Date of Patent: Feb. 26, 2019

(54) METHOD AND DEVICE FOR TREATING BIOMASS AND ORGANIC WASTE

(71) Applicant: CAMBI TECHNOLOGY AS, Asker (NO)

(72) Inventors: Paal Jahre Nilsen, Bødalen (NO); Hans Rasmus Holte, Reistad (NO)

(73) Assignee: CAMBI TECHNOLOGY AS, Asker (NO)

( * ) Notice: Subject to any disclaimer, the term of this patent is extended or adjusted under 35 U.S.C. 154(b) by 0 days.

(21) Appl. No.: 15/523,136

(22) PCT Filed: Oct. 29, 2015

(86) PCT No.: PCT/EP2015/075135
§ 371 (c)(1),
(2) Date: Apr. 28, 2017

(87) PCT Pub. No.: WO2016/066752
PCT Pub. Date: May 6, 2016

(65) Prior Publication Data
US 2017/0314046 A1    Nov. 2, 2017

(30) Foreign Application Priority Data
Oct. 29, 2014  (EP) .................................... 14190813

(51) Int. Cl.
  *C12P 7/10*   (2006.01)
  *C10G 3/00*   (2006.01)
  *C12M 1/00*   (2006.01)
  *C12M 1/34*   (2006.01)

(52) U.S. Cl.
  CPC .................. *C12P 7/10* (2013.01); *C10G 3/00* (2013.01); *C12M 41/40* (2013.01); *C12M 45/20* (2013.01); *C12M 47/02* (2013.01); *C12P 2201/00* (2013.01); *C12P 2203/00* (2013.01); *Y02E 50/16* (2013.01); *Y02P 30/20* (2015.11)

(58) Field of Classification Search
  CPC ..... C12P 7/10; C12P 2201/00; C12P 2203/00; C10G 3/00; C12M 41/40; C12M 45/20; C12M 47/02; Y02P 30/20; Y02E 50/16
  USPC ....................................................... 424/93.1
  See application file for complete search history.

(56) References Cited

U.S. PATENT DOCUMENTS

| | | | |
|---|---|---|---|
| 1,824,221 A | 9/1931 | Mason | |
| 2,690,426 A | 9/1954 | Moses et al. | |
| 2,759,856 A | 8/1956 | Saums et al. | |
| 4,461,648 A | 7/1984 | Foody | |
| 6,258,175 B1 | 7/2001 | Lightner | |
| 2009/0098616 A1 | 4/2009 | Burke et al. | |
| 2013/0152457 A1 | 6/2013 | Powell et al. | |

FOREIGN PATENT DOCUMENTS

| | | |
|---|---|---|
| JP | 2012-504935 A | 3/2012 |
| JP | 2014-158437 A | 9/2014 |
| WO | WO 98/27269 A1 | 6/1998 |
| WO | WO 00/14120 A1 | 3/2000 |
| WO | WO 01/60752 A1 | 8/2001 |
| WO | WO 03/013714 A1 | 2/2003 |
| WO | WO 2006/032282 A1 | 3/2006 |
| WO | WO 2007/009463 A2 | 1/2007 |
| WO | WO 2011/006854 A1 | 1/2011 |
| WO | WO 2013/013126 A1 | 1/2013 |
| WO | WO 2014/008364 A2 | 1/2014 |
| WO | WO 2014/039984 A1 | 3/2014 |
| WO | WO 2014/039986 A1 | 3/2014 |
| WO | WO 2014/070580 A1 | 5/2014 |

OTHER PUBLICATIONS

Chandel et al., 10. Detoxification of Lignocellulosic Hydrolysates for Improved Bioethanol Production, in Biofuel Production—Recent Developments and Prospects, Dos Santos Bernardes (Ed.), InTech (2011), pp. 225-246.*
Martín et al., "Comparison of the Fermentability of Enzymatic Hydrolyzates of Sugarcane Bagasse Pretreated by Steam Explosion Using Different Impregnating Agents," Applied Biochemistry and Biotechnology, vols. 98-100, 2002, pp. 699-716.
Palmqvist et al., "Fermentation of Lignocellulosic Hydrolysates. II: Inhibitors and Mechanisms of Inhibition," Bioresource Technology, vol. 74, No. 1, 2000, pp. 25-33.
Van Walsum et al., "Conversion of Lignocellulosics Pretreated with Liquid Hot Water to Ethanol," Applied Biochemistry and Biotechnology, vol. 57/58, 1996, pp. 157-170.
International Search Report for PCT/EP2015/075135 (PCT/ISA/210) dated Feb. 15, 2016.
Written Opinion of the International Preliminary Examining Authority for PCT/EP2015/075135 (PCT/IPE4/409) with transmittal (PCT/IPEA/416) dated Nov. 8, 2016.
Written Opinion of the International Searching Authority for PCT/EP2015/075135 (PCT/ISA/237) dated Feb. 15, 2016.

* cited by examiner

Primary Examiner — Jennifer M. H. Tichy
(74) Attorney, Agent, or Firm — Birch, Stewart, Kolasch & Birch, LLP

(57) ABSTRACT

The present invention provides a method for treatment of biomass material by fermentation, said method comprises a pre-treatment of the biomass material by thermal hydrolysis and wet explosion, resulting in an intermediate product having a dry matter concentration above 25% and temperature above 90° C. which is to be introduced to the fermentation, wherein a part of the content of the digestion tank used for the fermentation is recirculated and mixed with a part of the intermediate product from the pre-treatment.

18 Claims, 5 Drawing Sheets

METHOD AND DEVICE FOR TREATING BIOMASS AND ORGANIC WASTE

FIELD OF THE INVENTION

The present invention relates to methods, processes and devices for treatment of material of primarily organic origin, e.g. in the form of waste or biomass, by which the treated material's content of sugars and the like is rendered available for fermentation to one or more desired products.

BACKGROUND OF THE INVENTION

Municipal and industrial sludge and waste and other sources of waste-products of primarily organic origin such as by-products from gardening, agriculture, forestry, timber industry, food processing industries and the like, have over the years been the subject of increasing interest as possible starting materials for the production of $CO_2$-neutral fuels such as bioethanol or bio gas.

A number of different pre-treatment methods for biomass material by which the content of sugars and the like are made more available have been described in the literature. The most well-known are: Strong and weak acid hydrolysis; wet explosion (Steam Explosion—STEX); wet oxidation (WO); basic fiber explosion (Ammonia Fibre Explosion—AFEX); and thermal hydrolysis (Liquid Hot Water—LHW).

Typically strong and weak acid hydrolysis are characterised in that hemicellulose is hydrolysed and dissolved and the availability of cellulose is increased for a subsequent acid-based or enzymatic hydrolysis. When using these types of hydrolysis it is, after separation of the insoluble and the dissolved fractions, possible to process these fractions further among others by means of fermentation. Strong acid hydrolysis has among others been described by Lightner (U.S. Pat. No. 6,258,175), where also the possibility of re-using the applied acid after precipitation with ethanol is described. The primary purpose of the process is to dissolve cellulose and hemicellulose for subsequent use in e.g. production of ethanol by means of fermentation.

There are several problems connected with acid hydrolysis of biomass. Firstly it is necessary to divide the material to very fine particles (<1 mm), which is extremely energy demanding. Furthermore, a neutralization of the treated material is required, which is normally carried out by addition of $CaCO_3$ (limestone). This means that the consumption of chemicals in the process is high concurrently with a considerable amount of hydrated calcium sulphate being accumulated by the neutralization process. Moreover, the treated material from the acid hydrolysis has an inhibiting effect on enzyme hydrolysis and microbial fermentation compared to material resulting from other forms of treatment (see below). Finally, pumps, reactors and the like are exposed to corrosion as a result of the acid-catalysed process.

Wet explosion (STEX) was described as far back as 1928, where Mason developed the process for manufacturing hardboards (U.S. Pat. No. 1,824,221 and U.S. Pat. No. 2,759,856). The STEX process consists of thermal hydrolysis under high pressure, whereafter the pressure is released in a so-called "flash effect", where an explosion of each fibre takes place due to the great drop of pressure—hence the name wet explosion (or steam explosion). This method of treatment has later on been further developed for the manufacture of e.g. ethanol or paper (e.g., WO 98/27269).

In STEX normally a partial dissolution of hemicellulose (>80%) takes place, and cellulose is made available for subsequent hydrolysis. The effect of STEX resembles the effect of acid hydrolysis—however, the STEX process exposes the process equipment to far lesser wear and is not so demanding as regards the use of chemicals and accumulation of waste. However, in STEX there is still a considerable formation of substances that inhibit a possible subsequent fermentation process (Palmqvist and Hahn-Hägerdal 2000) particularly if the material previously has been liquified with acid ($SO_2$ or $H_2SO_4$ (Martin et al. 2002)).

Wet oxidation (WO) has been developed in order to oxidize organic waste fractions (U.S. Pat. No. 2,690,425) and has later on been modified so as to obtain a solution of hemicellulose from lignocellulose-containing biomass and organic waste (see e.g., WO 00/14120). Wet oxidation comprises a thermal process with addition of an oxidizing agent like an excess pressure of oxygen. In a wet oxidation the hemicellulose is partially dissolved and part of the present lignin is oxidized whereby the availability of cellulose is increased. Normally, WO does not require an extra process step for the removal of inhibiting substances.

Basic fibre explosion (AFEX) is a process that combines steam explosion and addition of a basic catalyst. In traditional AFEX the biomass is liquified in ammonia water at moderate temperatures (~50° C.), after which the pressure is momentary released (explosion). By this process cellulose and lignin are modified, which makes the cellulose more reactive (available), concurrently with release of the hemicellulose.

Thermal hydrolysis (LHW) is a process (typically 170° C.-230° C.) in which a high dissolution of hemicellulose takes place concurrently with a partial dissolution of lignin and an improved availability of cellulose (for enzymatic hydrolysis). Waste of sugar cane that has not previously been divided and that has been pre-treated with LHW, results in up to 90% of the theoretic ethanol yield after enzymatic hydrolysis and fermentation after addition of moderate amounts of enzyme (Van Walsum et al. 1996). U.S. Pat. No. 4,461,648 describes a method that increases the availability of cellulose- and lignocellulose-containing materials. The method comprises the addition of water steam under pressure, heat treatment and wet explosion, it is further described that a recycling of steam is not possible.

Known methods for production of $CO_2$-neutral fuels based on such organic waste or biomass often include a pre-treatment step employing some kind of Thermal Hydrolysis Process (THP) followed by an anaerobic digestion.

The processes are often based on a step of thermal hydrolysis performed in one or more reactor(s) using a combination of high temperature and high pressure to disintegrate the cellular structure of the organic material in the waste or the sludge and break down high molecular weight organic compounds into smaller molecules.

The step of thermal hydrolysis may be followed by a step of steam explosion performed in one or more pressure relief tank(s) where the content of the tank is disintegrated due to the quick relief of the pressure. The disintegration and splitting up of the biomass makes the following step of fermentation more effective.

The product resulting from pre-treatment steps employing a Thermal Hydrolysis Process (THP) will normally have a high temperature (e.g. above 90° C.) and be characterised by a relatively high dry matter content (e.g. above 25%) and in some instances also a relatively low pH (e.g. below 5). Thus, the handling of this product will normally require highly specialised equipment and in addition it will normally have to be subjected to cooling, neutralisation and/or dilution (e.g. with water) before introduction into a subsequent process based on anaerobic digestion, as this is usually performed at a lower temperature, at a lower dry matter content, and at neutral pH.

WO2007/009463 discloses a method for conversion of cellulosic material, to ethanol and other products. The cellulosic material is subjected to a hydrothermal pre-treatment by at least one soaking operation, a hydrothermal pretreatment in a pressurized reactor, and thereafter a pressing operation, creating a fiber fraction and a liquid fraction. The hydrothermal pretreatment leaves at least 80% of the lignin in the fiber fraction. Due to the need for the handling of material with high dry matter content highly specialized equipment will normally be required in the processes described in WO2007/009463.

WO03/013714 discloses a sluice system by which a product with high dry matter content may be portioned and then conveyed individually through at least one sluice chamber and two pressure locks, thereby allowing for e.g. transfer from a low to a high pressure zone.

Different improvements to the processes for treatment of biomass and organic waste described above have been developed over the years. Thus, one way of achieving these improvements has been by the use of recirculation. In particular recirculation of the steam otherwise used in the process and the use thereof to preheat the biomass, and recirculation of water effluent from the process to reduce the consumption of process water otherwise used in the process, has been described in the prior art.

WO2011/006854 discloses a method and a device for thermal hydrolysis and steam explosion of biomass. The method encompasses steps of preheating the biomass, leading the preheated biomass into at least two reactors where it is heated and pressurised by addition of steam, and finally a step-wise reduction of pressure using two pressure relief tanks. The preheating tank is preheated by return steam from the first and second pressure relief tanks.

WO01/60752 discloses a method, which is a continuous process, involving wet oxidation or steam explosion, for fermentatively converting biomass materials into ethanol. The fermentation wastewater effluent after separation from the produced ethanol, is subsequently subjected to an anaerobic fermentation step generating methane and a wastewater effluent wherein the amount of potentially inhibitory substances is at a sub-inhibitory level, permitting all or part of the effluent water to be recycled into the process to reduce the consumption of process water.

WO2014/039984 discloses a method for treating biomass to obtain monomeric sugars, wherein a pre-treated biomass is subjected to an enzymatic hydrolysis, and at least a portion of the liquefaction material from the enzymatic hydrolysis reactor is recirculated to a location upstream of the addition of the enzymes, as a portion of the coolant for the hot pretreated biomass.

US2009/0098616 discloses a method for treating plant material to release fermentable sugars. The method relates to a two-stage enzymatic hydrolysis process and is preferably preceded by an autohydrolysis step where the material is subjected to high temperature, steam and pressure preferably in the presence of acid. The low-viscosity effluent stream form the first hydrolysis stage is in part recirculated to the first enzymatic hydrolysis stage, some or all directly into the reactor, or it may be mixed with fresh lignocellulosic feedstock prior to entering the reactor. It is further disclosed that the enzymatic process may be performed under vacuum to remove volatile components, such as e.g. enzyme inhibiting compounds like furfural.

Despite the numerous methods of treatment for biomass material, there remains a need for a method where the biomass is pre-treated and subsequently fermented without the need for excess use of chemical additives or specialized equipment for handling dense material with a high dry-matter content, having a high temperature, and a relatively low pH. Additionally, there is a need for a method where dilution with water is minimized at the same time as energy-costs are reduced.

SUMMARY OF THE INVENTION

In a first aspect, the present invention relates to a method for treating a biomass material comprising at least the steps of:
pre-treatment of said biomass material comprising the steps of:
1) thermal hydrolysis at a temperature above 140° C., followed by
2) wet explosion resulting in an intermediate product having a dry matter concentration above 25% and a temperature above 90° C.,
subsequent fermentation of said intermediate product in a digestion tank,
and is further characterized in that said intermediate product is introduced into said digestion tank by mixing it into part of the content of said digestion tank being transported in a recirculation loop emerging from said digestion tank, wherein said mixing is performed before the mixture of said intermediate product and said part of the content of said digestion tank enters said digestion tank.

In a second aspect, the present invention relates to a device for treating a biomass material, wherein the device comprises:
one or more reactor(s), and
one or more pressure relief tank(s) connected to the reactor(s) for relief of pressure on the biomass, and
one or more digestion tank(s) connected to the pressure relief tank(s) for fermentation, wherein the digestion tank(s) is connected to the pressure relief tank(s) for recirculation of a part of the content of the digestion tank to be mixed with a part of the content of the pressure relief tank(s).

None of the herein above-mentioned improvements involving recirculation, overcomes the need for highly specialised equipment to handle the further processing of products resulting from conventional pre-treatment steps employing a Thermal Hydrolysis Process having a high temperature (e.g. above 90° C.), a relatively high dry matter content (e.g. above 25%) and a relatively low pH (e.g. below 5).

In contrast the method and device according to the present invention uses recirculation of part of the material being fermented to overcome the above-mentioned normal need for specialised equipment, cooling, neutralisation and/or dilution (e.g. with water).

SHORT DESCRIPTION OF THE DRAWINGS

Figure 3:
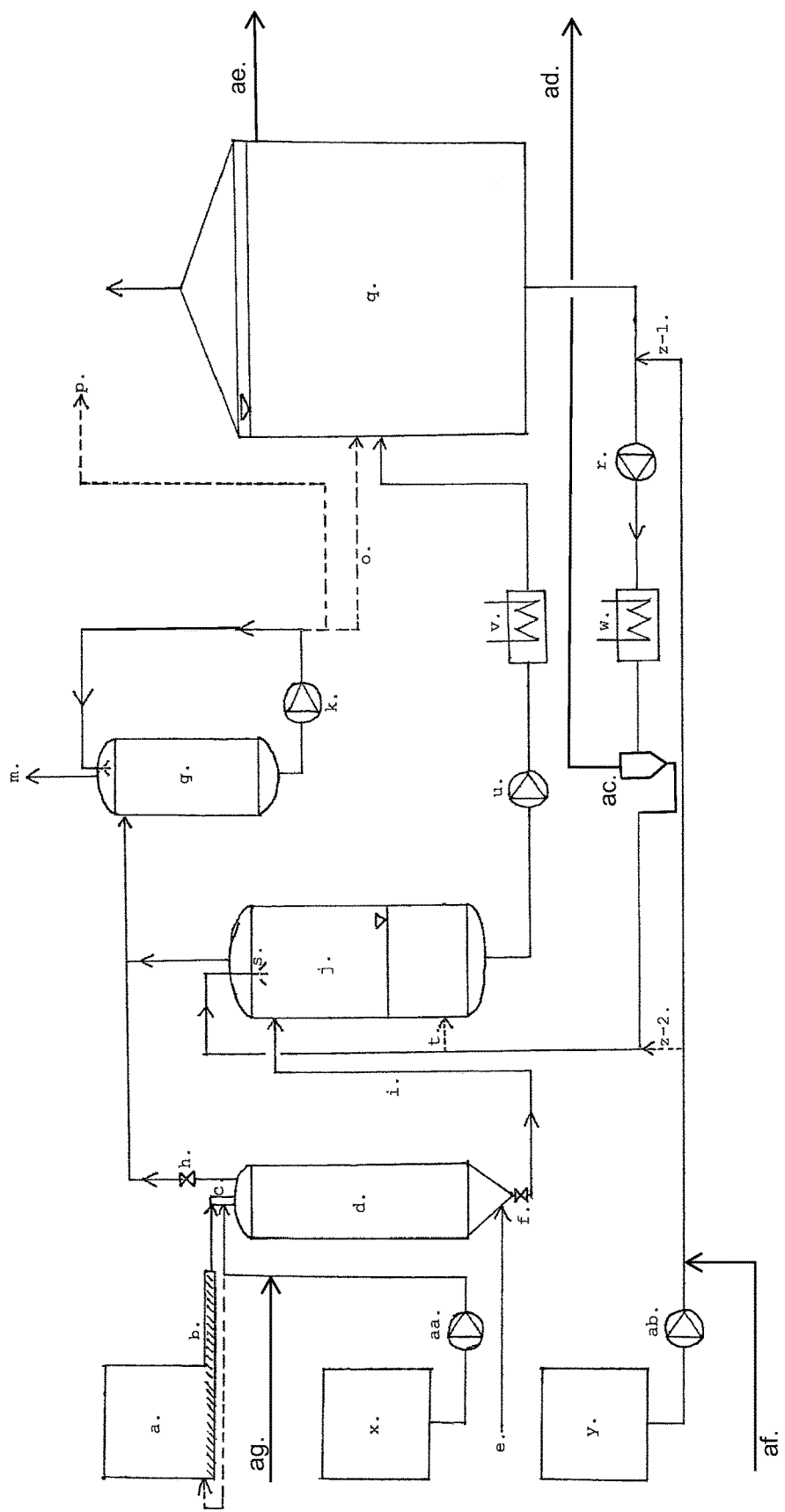

FIG. 3 shows (schematically) an embodiment of the present invention for first pretreating biomass by thermal hydrolysis (d) and wet explosion (j) and subsequently fermenting the intermediate product obtained thereby in a digestion tank (q), wherein part of the content of the digestion tank is transported in a recirculation loop (t) into the pressure relief tank (j), the embodiment includes an optional feature of flashsteam being led to a condenser (g) and a circulation pump (k), and options for leading condensate to downstream digestion tank (q) or to further processing for recovery of chemicals (p).

Figure 4:
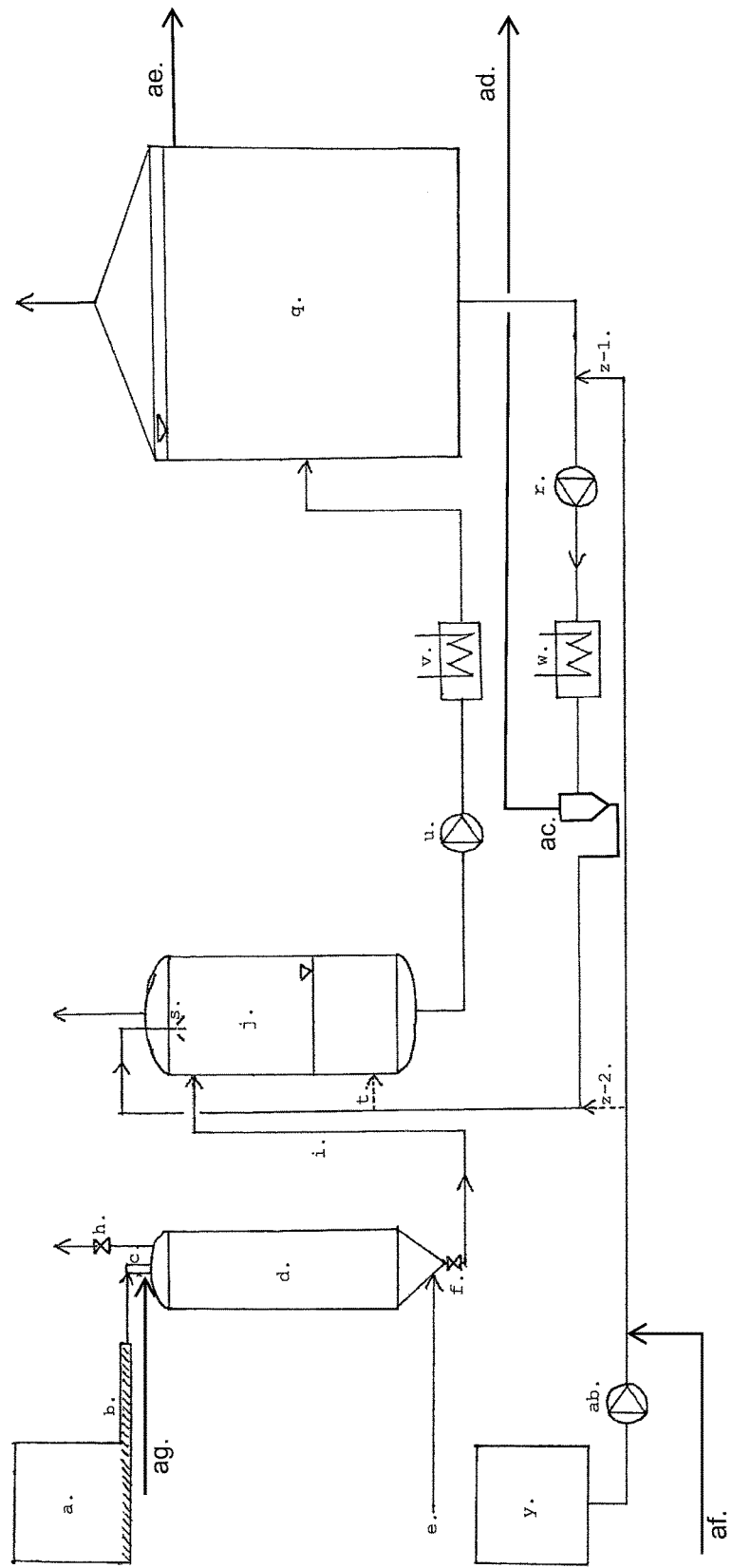

FIG. 4 shows (schematically) an embodiment of the present invention for first pretreating biomass by thermal hydrolysis (d) and wet explosion (j) and subsequently fermenting the intermediate product obtained thereby in a digestion tank (q), wherein part of the content of the digestion tank is transported in a recirculation loop (t) into the pressure relief tank (j).

Figure 5:
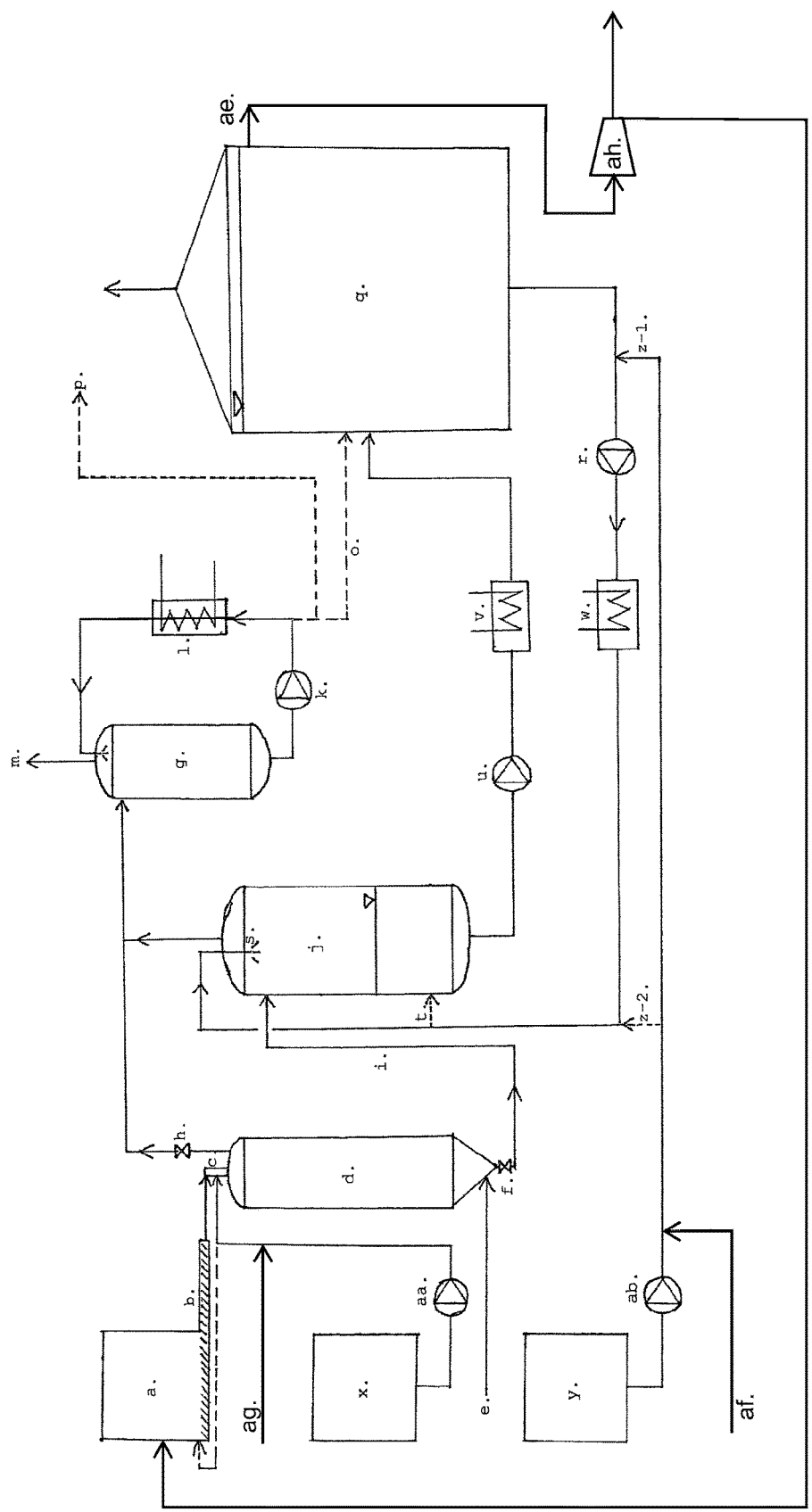

FIG. 5 shows (schematically) an embodiment of the present invention, in which part of the content of the digestion tank (q) is dewatered (ah) and returned as so-called dewatered cake having an increased dry matter content to the feed line (a) for the thermal hydrolysis reactor (d) thereby mixing it together with the biomass material otherwise feed into the process.

DETAILED DESCRIPTION OF THE INVENTION

The present invention relates to a method for treating a biomass material comprising at least the steps of:
pre-treatment of said biomass material comprising the steps of:
1) thermal hydrolysis at a temperature above 140° C., followed by
2) wet explosion, resulting in an intermediate product having a dry matter concentration above 25% and a temperature above 90° C.,
subsequent fermentation of said intermediate product in a digestion tank,
and is further characterized in that said intermediate product is introduced into said digestion tank by mixing it into part of the content of said digestion tank being transported in a recirculation loop emerging from said digestion tank, wherein said mixing is performed before the mixture of said intermediate product and said part of the content of said digestion tank enters said digestion tank.

The content of dry matter in the material resulting from a THP-like process is usually very high, sometimes above 90%. When the dry matter content is above 25% a problem arises when using conventional equipment and devices, because the intermediate product cannot be transported to the digestion tank through standard pipes and employing standard pumping equipment. Thus, highly specialised equipment, such as pipes with screw, spiral or helical conveyers, is needed and due to the relatively low pH and high temperature and dry matter content of the material, and whatever equipment employed will need frequent maintenance and repairing. Thus, one advantage resulting from the method according to the invention is that the material with a high dry matter content, which would according to the traditional methods need to be transported by specialised equipment, is now mixed with a recirculating flow from the down-stream digestion tank. As the content of the digestion tank has a lower dry matter content and a lower viscosity, the mixed flow has a relatively lower content of dry matter and viscosity and therefore becomes applicable for easy transportation through standard pipes and employing standard pumping equipment.

Scaling, caking and sometimes blockage inside vessels, pipes and especially heat exchangers/coolers is a known problem during thermal treatment of certain materials, especially organic materials rich on lignin, resins and the like. Reduced capacity and operational challenges may become critical for the operation of such plants. Frequent use of cleaning in place systems may be required to maintain operability and the use of alkaline cleaning chemicals are commonly used. The biodegradation taking place in down-stream anaerobic digestion process (fermentation) degrades organic acids and establishes a relatively alkaline environment with an alkali fluid. An additional advantage of the present invention is that the vessels, pipes, valves and coolers benefit from the recycling of the digested material providing a continuous alkaline cleaning without adding additional chemicals during normal operation. For most feedstocks, this process eliminates the use of clean-in-place (CIP) chemicals. For the most difficult feedstocks, the consumption of additional cleaning chemicals will be substantially reduced.

The behavior of fibre and cellulosic material is influenced by several factors. The present inventors have found that one of the factors influencing on the ability to keep fibres in suspension is pH. Low pH that arises as a result of thermal pre-treatment of the organic materials makes it difficult to keep the fibers in suspension, thus clogging becomes a major problem. A major advantage of the recirculation according to the present invention is that the alkaline digestate increases pH whereby the behavior of the fibres and cellulosic material is changed keeping it in suspension and allowing it to be pumped to downstream processes without the use of conveyer systems.

The present inventors have specifically found that the pH obtained during the fermentation—in the digestion tank—typically being in a range of pH 7.3-8.3 is beneficial for fiber wettability and transport properties. The fully or in part hydrolysed biomass fibers, as for instance obtained from a wet explosion, has a tendency to separate from the remaining intermediate product at low pH, for instance a pH below 6. Accordingly, by recirculating part of the content of the digestion tank and mixing with the product from the wet explosion, it is possible to increase the pH-value of the otherwise slightly acidic intermediate product and keep the fully or in part hydrolysed biomass fibers dissolved.

In a specific embodiment of the invention the pH of the feed to the digestion tank obtained after mixing the intermediate product with recirculated fermentation product is above pH 6; in a preferred embodiment the pH of the feed to the digestion tank after mixing is above pH 6.5.

According to one embodiment of the invention, the above-mentioned intermediate product has a temperature above 100° C.

In such cases, i.e. involving an intermediate product with a temperature above 100° C., additional advantages may be achieved, because the steam, that would normally accompany such an intermediate product when being the result of a THP-like process, can then be used to either heat or even pasteurise other process streams comprising materials of organic origin that are to be added to the pre-treated material prior to digestion, e.g. liquid manure.

In a further embodiment of the invention, the above-mentioned intermediate product has a pH below 5.

The intermediate product resulting from a thermal hydrolysis pre-treatment is often acidic (e.g. with a pH 4-5). Thus, apart from the fact that such a product will normally have to be subjected to separate neutralisation requiring the use of chemicals before introduction into a process based on anaerobic digestion, the transportation of acidic material from the pre-treatment process to the digestion tank may furthermore involve specialized equipment. However, in the method according to the invention at least part of the neutralization of the intermediate product may be achieved concomitantly with the recirculation from the digestion tank. Thereby achieving additional advantages in relation to the lowered need for chemical neutralization and/or specialized equipment otherwise employed in the transporting of acidic material. In one embodiment of the invention the intermediate product is neutralized by mixing with the recirculated material from the digestion tank. The method of the invention may be adjusted so that the more acidic the intermediate product is, the more digestate is to be recirculate in order to obtain an optimal pH range.

As a further benefit, the process according to the invention may be performed in a closed system. Thereby, the surroundings will benefit from not being subjected to volatile compounds otherwise likely to evaporate from the material undergoing pre-treatment and subsequent fermentation in the digestion tank, and which may be both potentially hazardous and smell very badly.

The thermal hydrolysis pre-treatment may typically be performed batch-wise. A continuous-like process flow is possible downstream from the thermal hydrolysis, therefore it is possible to handle, capture and make use of the relatively large amount of steam released from the wet explosion (i.e. in cases where the material has a temperature above 100° C.), which further result in that the external energy consumption for the total process is minimized.

According to the invention, the recirculation from the digestion tank to the pressure relief tank(s) may preferably be a continuous process flow. As the thermal hydrolysis feeding the pressure relief tank preferably may be a batch-wise process, the hydrolysate level in the pressure relief tank will in this scenario vary. When the method of the invention is applied in this manner the pressure relief tank further functions as a buffer storage tank, whereby a continuous process flow to the downstream digestion tank, and the fermentation process therein is obtained.

For large-scale equipment it is favorable to include more than one reactor for the thermal hydrolysis pre-treatment. In this manner, it is possible to run several batches with delayed cycles, whereby both the output to the pressure relief tank(s) is distributed over time, as well-as the required steam input for heating the reactors is distributed more evenly. The latter is favorable for the dimensioning of the steam production facilities and energy demand thereto. In this manner a semi-continuous flow to the pressure relief tank(s) may be obtained. Additionally, a further advantage of including more than one reactors for the thermal hydrolysis step, is the upstream advantage of an increase in continuity in the feeding of the thermal hydrolysis tanks with biomass from the biomass storage tanks.

In one embodiment of the invention, the return steam from the wet-explosion step performed in one or more pressure relief tank(s) may be used to pre-heat the biomass in a pre-heating tank before the biomass is pumped to the reactor(s). Steam is additionally supplied to the reactor(s) during and after filing of the biomass to heat this up to a desired temperature. The need for adding fresh steam to the reactor(s) is thereby reduced.

The intermediate product resulting from the pre-treatment, i.e. thermal hydrolysis and wet explosion, of the biomass material will normally have a dry matter concentration above 25% and a temperature above 90° C. Conventionally, the transportation of the intermediate product having high dry matter content is solved by highly specialised equipment. Furthermore, the temperature of the intermediate product is conventionally lowered by traditional cooling water. The present invention is based on recirculation of at least part of the content of the digestion tank(s), thereby eliminating the disadvantages resulting from the otherwise necessary treatment of the intermediate product before this can enter the digestion tank. The pre-treatment of the biomass material may be done in various ways as described below.

A number of different pre-treatment methods for biomass material by which the content of sugars and the like are made more available have been described in literature, some of which are mentioned herein in the background section. The most well-known are: strong and weak acid hydrolysis, wet explosion, wet oxidation (WO), ammonia fiber explosion (AFEX), thermal hydrolysis (Liquid Hot Water—LHW) and combinations thereof. These treatments may either alone or in any combination be part of the pre-treatment according to the invention. Depending on the choice of pre-treatment, the method of the present invention may further comprise a pre-treatment step of full or partial grinding of the biomass.

Further details of the pre-treatment steps is described below:

Thermal Hydrolysis

The biomass and/or organic waste material is introduced to a reactor, where the material is mixed and heated with direct or indirect steam to a temperature above 140° C., typically in a range from 140-220° C., preferably in a range from 140-200° C., more preferably 150-190° C., even more preferably 160-180° C. and most preferably 170° C., at saturation pressure. When the desired temperature and the desired pressure have been reached, the material may be maintained under these conditions for 5-30 min, preferably 10-25 min, more preferably 10-20 min and most preferably 15-20 min.

In one specific embodiment of the invention, the thermal hydrolysis is performed at a temperature above 140° C. and maintained for 5-30 minutes followed by, wet explosion carried out by means of reducing the pressure from 5-35 bar to atmospheric pressure.

Wet Oxidation

In one embodiment of the invention, the method furthermore comprises a wet oxidation, which oxidation preferably may be performed after the thermal hydrolysis step but before the wet explosion. After termination of the thermal hydrolysis an appropriate oxidizing agent may be added to the material, preferably oxygen, hydrogen peroxide or air, in an amount that may depend on the content of lignin and that typically corresponds to 2-20% of the COD (chemical oxygen demand) content of the material, preferably 3-19%, more preferably 5-17%, such as preferably 7-16%, more preferably 8-15%, such as preferably 9-14%, more preferably 10-13% and determined by the pressure development in the reactor. The wet oxidation may typically be carried out at a temperature in a range of 170-220° C.

Pressure and temperature may be increased in connection with the wet oxidation to 15-35 bar, preferably 20-35 bar, more preferably 25-35 bar and most preferably 30-35 bar and 170-210° C., preferably 180-200° C., more preferably 190-200° C. respectively. In one embodiment the oxidation is at a pressure above the saturation pressure in the thermal hydrolysis of step 1). When the desired pressure and the desired temperature have been reached after the addition of the oxidizing agent, these conditions may be maintained for 1-30 min, preferably 5-25 min, more preferably 10-20 min and most preferably 15-20 min. Optionally, after termination of the wet oxidation reaction the pressure of the material may be partially released to 5-10 bar. In that case, the pressure interval at which the subsequent wet explosion can be performed, is 5-35 bar. If no partial release of pressure is performed, then the pressure interval is 1-35 bar.

In a specific embodiment of the invention, the method comprises an oxidation at a pressure of 15-35 bar and a temperature of 170-220° C. which is maintained for 1-30 minutes. In a more specific embodiment of the invention, the method comprises an oxidation at a pressure of 15-35 bar and a temperature of 170-210° C. which is maintained for 1-30 minutes, which oxidation is in a further preferred embodiment performed after the thermal hydrolysis but before the wet explosion.

Wet Explosion

After termination of the thermal hydrolysis step, and optionally a wet oxidation step, the treated biomass material is hereafter led to one or more pressure relief tank(s), during which the pressure is reduced from 5-35 bar; the pressure may typically be reduced to a pressure below 2 bar, preferably below 1.5 bar. Preferably the pressure is reduced from 15-35 bar to approximately 1 bar, i.e. atmospheric pressure. During this wet explosion most cell structures are disintegrated. Immediately after the wet explosion the temperature of the oxidized material is preferably 95-110° C. rendering the material sterile. When the thermally treated material is discharged from the thermal hydrolysis reactor, the discharge to one or more pressure relief tank(s) is driven by the pressure difference between the reactor and downstream pressure relief tank(s). Due to the pressure drop, condensed steam will flash off inside the pressure relief tank(s). The wet explosion takes place via one pressure relief tank or sequentially in two or more pressure relief tanks. The term 'flash tank' and the term 'pressure relief tank' are used interchangeable herein.

Fermentation

After cooling to the desired temperature, the treated material can be further processed to ethanol, hydrogen, lactic acid, methane, succinate, organic acids or other desired products by fermentation.

The overall processes of the present invention may also encompass a treatment with enzymes (e.g. cellulases) in order to convert the carbohydrates to monohydrates before fermentation into ethanol or other fermentation products.

Subsequently to the pre-treatment the slurry and/or the aqueous phase therefrom may further be subjected to an enzymatic hydrolysis treatment resulting in at least partial hydrolysis of the cellulose and hemicellulose to obtain a slurry and/or aqueous phase containing an amount of microbially fermentable sugars.

The purpose of such an enzymatic hydrolysis treatment is to hydrolyse oligosaccharide and possibly polysaccharide species produced during a wet oxidative treatment, if any, and/or steam explosion of cellulose and/or hemicellulose origin to form fermentable sugars (e.g. glucose, xylose and possibly other monosaccharides).

In one embodiment of the present invention the method further comprises an enzymatic hydrolysis of said intermediate product, the enzymatic hydrolysis is performed prior to the fermentation step but may be performed prior to or after the mixing of said intermediate product with a part of the content of said digestion tank. In a preferred embodiment the method do not comprise any separate enzymatic hydrolysis step.

Enzymatic hydrolysis may be achieved in a known manner by treatment with one or more appropriate carbohydrase enzymes (glycosidases, EC 3.2). In a preferred embodiment, the carbohydrase enzyme is selected from the group consisting of a cellulase (EC 3.2.1.4) in the case of hydrolysis of cellulose or cellulose fragments; a xylanase (such as an endo-1, 4-β-xylanase, EC 3.2.1.8) in the case of hydrolysis of xylans; a β-glucanase including a glucan-1, 3-β-glucosidase (exo-1, 3-β-glucanase, EC 3.2.1.58) or an endo-1, 3(4)-β-glucanase, EC 3.2.1.6, in the case of hydrolysis of soluble fragments of cellulose to glucose, and a pectinase (polygalacturonase, EC 3.2.1.15) in the case of hydrolysis of pectate and other galacturonans. Commercial enzyme products of relevance in this connection include Celluclast™, available from Novo Nordisk A/S, Bagsværd, Denmark, e.g. as Celluclast™ 1.5 L (a liquid preparation). Celluclast exhibits both cellulase activity (degrading cellulose to glucose, cellobiose and higher glucose polymers) and some degree of xylanase activity.

Fermentable sugars, notably monosaccharide product(s), obtained by hydrolysis are useful for further transformation to give other useful products (e.g. ethanol or xylitol). Thus, glucose (derived from cellulose) and xylose (derived from xylans in hemicellulose) may be transformed to ethanol using relevant fermenting microorganisms as described herein, and xylose may, for example, alternatively be transformed to xylitol by established methods (e.g. by catalytic hydrogenation or by fermentation).

In the method according to the invention the intermediate product is subjected to fermentation in one or more digestion tank(s). The fermentation step may employ one or more fermenting microorganisms capable of degrading oligo- and/or monosaccharides present in said liquid phase to form ethanol.

With regard to fermentation of, e.g., glucose to yield ethanol, any microorganism capable of converting glucose to ethanol may be used in the process according to the invention. For example, a suitable microorganism include a mesophilic microorganism (i.e. one which grows optimally at a temperature in the range of 20-40° C.), e.g. a yeast also referred to as "baker's yeast", *Saccharomyces cerevisiae*.

With regard to fermentation of, e.g. xylose to yield ethanol, any microorganism capable of converting xylose to ethanol can be used in the process according to the invention. Useful microorganisms include e.g. certain types of thermophiles (i.e. organisms which grow optimally at an elevated temperature—normally a temperature in excess of about 50° C.) and genetically engineered microorganisms derived therefrom. In preferred embodiments, a suitable organism for the ethanol fermentation is selected from the group consisting of *Thermoanaerobacter* species including *T. mathranii*, *Zymomonas* species including *Z. mobilis* and yeast species, such as *Pichia* species. An example of a useful strain of *T. mathranii* is described in Sonne-Hansen et al., 1993 or Ahring et al. 1996 where said strain is designated as strain A3M4.

It will be appreciated, that a useful ethanol-fermenting organism can be selected from a genetically modified organism of one of the above useful organisms having, relative to the organism from which it is derived, an increased or improved ethanol-fermenting activity. As used herein the expression "genetically modified bacterium" is used in the conventional meaning of that term i.e. it refers to strains obtained by subjecting a organism to any conventionally used mutagenization treatment including treatment with a chemical mutagen such as ethanemethane sulphonate (EMS) or N-methyl-N'-nitro-N-nitroguanidine (NTG), UV light or to spontaneously occurring mutants, including classical mutagenesis. Furthermore, as it is possible to provide the genetically modified bacterium by random mutagenesis or by selection of spontaneously occurring mutants, i.e. without the use of recombinant DNA-technology, it is envisaged that mutants of the above mentioned organism can be provided by such technology including site-directed mutagenesis and PCR techniques and other in vitro or in vivo modifications of specific DNA sequences once such sequences have been identified and isolated.

Using microorganisms with different optimal growth temperature requirements to ferment glucose and xylose, respectively, to yield ethanol, it may thus be desirable to perform the fermentation step in question as a two-stage process wherein the slurry and/or aqueous phase after the preceding steps is first contacted with one of the microorganisms under appropriate conditions therefore (e.g. *S. cerevisiae* at a temperature of around 30° C.) and subsequently with the other microorganism under its appropriate conditions (e.g. *T. mathranii* at a temperature of about 70° C.). In the present invention the recirculation of part of the content of the digestion tank may be done with content from either one, or both of the two stages. In cases where an increased cooling capacity is desirable, the recirculation may preferably be done from the first, less warm, stage. The two stages may suitably take place in separate fermentation reaction vessels or in the same reaction vessel in a sequential manner.

As opposed to an enzymatic hydrolysis having a well-defined process and being dependent on e.g. temperature, pH and the amount of added enzyme, a fermentation reaction is more critical in the sense that the proper growth conditions needs to be present for the selected microorganism. Additionally, the growth medium—in the present case the pre-treated biomass material—need to be kept in balance with regard to e.g. nutrients and toxic or inhibitory substances. Important balances are, among others, the C:N ratio, the NPK balance, the S content and the content of critical micronutrients. Some biomass materials may as a starting point comprise low of components such as but not limited to Selenium, Molybden and Cobalt. Thus, especially unilateral biomass materials may as a starting point comprise low amounts of certain critical components required for optimized fermentation. In such cases, balancing the original material with complementing biomass materials will be beneficial and the present invention thus also allows for processes based on mixed biomass materials. In case a balanced material cannot be achieved, addition of micronutrients may be required based on analysis of actual nutrient balance during the fermentation. If required, nutrients solutions can be added through an injection point placed on a circulation circuit, or by adding nutrients directly into the material feed into the fermentation reaction vessel, depending on the type of nutrient mixture deemed to be required based on a micronutrient analyses of the fermented material. Chemicals may also be added in order to bind certain components that would otherwise inhibit the process if present in high concentrations. An example of such a component is sulphur, which may in certain processes inhibit the intended fermentation process if present in high concentrations, but which may be removed by the addition of FeCl solution in order to bind the Sulphur as IronSulphate.

With regard to the present invention, it is especially notable that an enzymatic hydrolysis typically produces a hydrolysate having a pH of between 4 and 6. A fermentation of biomass material, having been pre-treated by first a thermal hydrolysis and then a wet explosion, on the other hand, gives a fermentation product having a pH typically in a range of 7-8.5; preferably in a range of pH 7-8.3; and more preferably in a range of pH 7.3-8.3. As will be evident from these differences in pH, the herein above described advantages of fiber wettability, dissolution and hence increased transport properties according to the present invention are only obtained by recirculating part of the digestion tank content to the product from the wet explosion, and would not likewise be obtained by any potential recirculation from an enzymatic step. Due to the recirculation loop from the digestion tank, the method of the present inventions provides an increased pH of the feed to the digestion tank. In a specific embodiment of the invention the pH of the feed to the digestion tank obtained after mixing the intermediate product with recirculated fermentation product is above pH 6; in a preferred embodiment the pH of the feed to the digestion tank after mixing is above pH 6.5.

Some of the process parameters influencing a fermentation process is the solid retention time (SRT) and the hydraulic retention time (HRT). The latter being a measure of the average length of time a soluble compound remains in the digestion tank. By introducing a separation step on a circulation circuit from the fermentation vessel as presented in the accompanying figures the SRT and HRT can be made significantly different for a fermentation process. In the method of the present invention the fermentation may typically be performed as a continuous process having a HRT of 10-40 days, preferably 15-30 days and a SRT of 10-40 days, preferably 20-40 days ensuring a longer exposure of and thus an increased Volatile Solids Reduction (VSR) of hard degradable solids present in the biomass material. In one embodiment of the invention the fermentation is a continuous process having a HRT of between 2 and 20 days; preferably between 10 and 20 days; more preferably between 15 and 17 days In a further embodiment of the invention the fermentation is a continuous process having a SRT of between 15 and 40 days; preferably between 20 and 40 days, and more preferably between 30 and 40 days. By its very nature the efficiency of the above-mentioned separation step is important for the resulting difference between HRT and SRT. On the other hand a high degree of separation may also be energy consuming which may not be beneficial for all applications. Hydrocyclones designed for the purpose is normally sufficient to achieve a beneficial improvement of the difference between HRT and SRT at an acceptable effort and typically enables an increase in the solid retention time (SRT as compared to HRT) of 5-30% depending on the specific substrate and process parameters.

In a further embodiment of the present invention tests have revealed a positive effect of performing the hydrolysis in two stages. Thus, in a preferred embodiment of this innovation part of the content of the fermentation vessel may be dewatered and returned as so-called dewatered cake having an increased dry solid (DS) content to the feed line for the hydrolysis step thereby mixing it together with the biomass material otherwise feed into the process in a or x in the accompanying figures. The dewatering may be done in position ac or ah, or alternatively in a downstream dewatering. Parts of the material may than be re-feed into the process at an appropriate position in order to achieve a two-stage hydrolysis of hard degradable solids present in the biomass material. Such an embodiment of the invention is illustrated in the accompanying FIG. 5. The dewatering may take place in a centrifuge, belt thickener, belt press, filterpress, screw press or any other adequate dewatering machine. Combination of different dewatering machines such as gravity belt thickener and screw press may add significant potential for reduced electricity consumption compared with conventional centrifuges. Reduced electricity consumption may be in the area of ½-⅙ of the electricity consumption of a decanter centrifuge.

Fermentation reaction vessels (digestion tanks/fermentors) of any suitable, known type may be employed in performing one or more fermentation steps of the type in question. For further details of suitable reaction vessels, reference may be made, for example, to J. E. Bailey and D. F. Ollis, 1986. Batch fermentation and continuous fermentation are both suited in this connection. The terms 'fermentation reaction vessel', 'digester' and 'digestion tank' are used interchangeable herein.

Subsequent to the ethanol fermentation step, the ethanol is separated from the fermentation medium.

Recycling

As described previously herein, the method of the invention uses a recycle flow from the content of the digestion tank, in which part of the content from the digestion tank is recycled to the ultimate step of the pre-treatment and hence mixed with the intermediate product. The ultimate step of the pre-treatment being the wet explosion, or optionally any further pre-treatment steps performed on the biomass material.

The flow of material from the digestion tank is preferably considerably higher, typically 3-30, preferably 5-25, times, than the flow of pre-treated material resulting from the ultimate step of the pre-treatment (thermal hydrolysis, wet-explosion and optionally further pre-treatment like wet oxidation). In this way the resulting mixed flow entering the digestion tank will have a pH, temperature and dry matter content, which is compatible with the normal working process parameters of the digestion tank. Furthermore, dry matter and thus viscosity will be adjusted through balancing the recirculation by recycling 3-30 times with digestate. However, the recirculation in itself does not influence the average dry mater content of the feed coming from the thermal hydrolysis reaction. Instead the dry matter content may be adjusted by dilution with water in the manner as for instance described in FIGS. 3, 4, and 5, prior to the thermal hydrolysis (ag) or via the recirculation loop into the pressure relief tank (af).

According to an embodiment of the invention, the part of the content of the digestion tank is mixed with the part of the intermediate product in a way that at least 10 parts (volume) of the content of the digestion tank is mixed with one part (volume) of the intermediate product, preferably at least 20 parts (volume) of the content of the digestion tank is mixed with one part (volume) of the intermediate product.

The mixing can be achieved by providing the flow from the individual pipes into a mixing tank or directly to a common pipe. The mixing may be achieved by additional mixing means.

The recirculation may for instance be performed by injecting the content from the digestion tank into the pressure relief tank below liquid level, whereby efficient mixing at the same time is obtained. Alternatively, the recycled stream from the digestion tank may be led to the top of the pressure relief tank, e.g. through a nozzle, whereby the recycled stream at the same time serves as a quench for condensation of flash steam inside in the pressure relief tank.

In a preferred embodiment of the invention the mixing takes places in the pressure relief tank; as one of the major advantages of the recycling step is the increased fiber wettability and transport properties after the wet explosion. Hence by carrying out the mixing directly after the wet explosion but prior to any transportation of the intermediate product the greatest benefit is obtained. However, a later stage mixing is also possible.

The mixing of 10 parts (volume) of the content of the digestion tank with one part (volume) of the intermediate product should be understood as mixing the two products in volume ratio 10:1; preferably the volume ratio is in a range of 3:1-30:1 depending of feed characteristics, and measured at same pressure and temperature.

By the wording 'the content of the digestion tank' is meant the liquid and/or the aqueous slurry resulting from the fermentation, but before the separation of the fermentation product e.g. ethanol.

By the wording 'the intermediate product' is meant the liquid and/or the aqueous slurry resulting from the pre-treatment, but before the fermentation.

By the term 'a part of the content' is to be understood a partial amount or the whole amount of the liquid and/or the aqueous slurry.

In an embodiment according to the invention, the one part (volume) of the intermediate product is introduced to the mixing with a flow of at least 5 $m^3/h$, preferably at least 10 $m^3/h$. The flow of the content from the digestion tank or the intermediate product is measured in $m^3/h$ at 25° C. and 1 bar.

The biomass material may be chosen from the group consisting of straw, wood, fibres, baits, paper pulp, and waste streams; or from by-products from other processing industry such as food processing industry, energy crops, leaves, branches, slurry and household waste or other similar materials applicable in the production of ethanol or other biological products. Preferably the biomass material is selected from biomass rich on cellulose and/or hemicellulose. Beneficial results are specifically achieved on straw, wood-based fibres and energy crops, suck as e.g. maize. In one preferred embodiment of the invention the biomass material is selected from the group consisting of straw, wood-based fibres and energy crops, such as e.g. maize.

Typically the biomass introduced to a method according to the invention may have a dry-matter content of 50-80%. In one embodiment according to the invention, the biomass material introduced to the process has a dry matter concentration above 25%, preferably above 50%, and more preferably above 75% by weigh. By the percentage of the dry matter content or concentration is meant the weight percentage, i.e. % (w/w).

According to one embodiment of the invention, the intermediate product has a dry matter concentration above 25% by weight, preferably above 30%, more preferably above 35%, and most preferably above 40%. By intermediate product is hereby meant the pre-treated product (thermal hydrolysis and wet explosition) prior to any mixing with recirculated content from the digestion tank or any further dilution by water after said pre-treatment steps.

Depending on the applied biomass material, the method according to the invention may further comprise one or more dilution step(s). Dilution of the biomass material or the intermediate product may take place at several points during the method. For instance, dilution may take place prior to the thermal hydrolysis, e.g., by introducing water to the thermal hydrolysis reactor; or upstream of the thermal hydrolysis reactor, e.g. by introducing water into the recirculation loop entering the pressure relief tank or directly into the pressure relief tank. The latter option allows for use of the dilution water to at least in part quench the flash steam. Dilution of the dry matter content may additionally be regulated by the volume ratio of recirculated material from the digestion tank, as the dry matter content in the digestion tank is much lower.

In a preferred embodiment of the invention, dilution is performed via the recirculation loop or directly into the pressure relief tank.

Dilution, if necessary, aid in controlling the dry matter content in the feed to the digestion tank and thus the loading rate. The loading rate for the digestion tank may typically be in a rage of 2-10 kg VS/m$^3$/day (VS=volatile solids), and may preferably be in a range of 3-6 kg VS/m$^3$/day. Different feed material may provide different viscosities and the loading rate may be adjusted accordingly. Traditionally the biomass viscosity is one of the limiting factors for the loading rate, however, the present invention significantly improves the fiber wettability and transport properties allowing for a higher loading rate.

The low-temperature flow from the digestion tank may furthermore be used to condense the gas phase from the pressure relief tank giving the additional advantage of being able to recycle otherwise lost beneficial components, e.g. volatile acids, from the gas phase to the digestion tank. Furthermore, undesired components, such as e.g. furfurals, may in this manner be extracted and separated from the gas phase to avoid inhibition of downstream digester, or for subsequent external purification and use, or to oxidize for heat recovery.

Condensation of the gas phase from the pressure relief tank(s), bringing the gases in a liquid state, may be achieved by using a part of the liquid and/or the aqueous slurry resulting from the fermentation as a cooling medium.

According to one embodiment of the invention, a part of the gas phase from the pre-treatment is condensed by using a part of the content of the digestion tank as cooling medium.

By the wording 'a part of the gas phase' is meant a partial amount or the whole amount of the gas phase in the pressure relief tank(s).

In one embodiment of the invention, furfurals in the condensed gas phase are separated by extraction. Furfural is also known as furan-2-carbaldehyde. Other names are e.g. furan-2-carboxaldehyde, fural, furfuraldehyde, 2-furaldehyde, and pyromucic aldehyde.

In an embodiment of the invention, the volatile acids from the gas phase in the pressure relief tank(s) is condensed and thereafter recycled to the digestion tank(s) where they are useful in the fermentation. By volatile acids is meant acids with low boiling point such as carbonic, acetic and butyric acid.

The invention also relates to a device accomplishing the same advantages as described for the method according to the invention.

The second aspect the invention relates to a device for treating biomass material, wherein the device comprises:
one or more reactor(s), and
one or more pressure relief tank(s) connected to the reactor(s) for relief of pressure on the biomass, and
one or more digestion tank(s) connected to the pressure relief tank(s) fermentation, wherein the digestion tank(s) is connected to the pressure relief tank(s) for recirculation of a part of the content of the digestion tank to be mixed with a part of the content of the pressure relief tank(s). The herein mentioned 'reactor(s)' may also be termed 'thermal hydrolysis reactor(s)'.

The digestion tank includes an outlet which may be from the top surface, side, or bottom for most applications, as the skilled person will know. However, for some types of feed material it may be beneficial to have different solid retention time (SRT) and hydraulic retention time (HRT). This may be obtained by including one or more separator(s) or thickener(s) to a device according to the invention.

The method and device according to the invention may further comprise one or more separator(s) or thickener(s), preferably one or more hydrocyclone separator(s), connected to the recirculation loop from the digestion tank(s) for separation of solids, having one outlet with increased dry matter content and one outlet with lower dry mater content, the outlet with increased dry matter content may be led back to the digestion tank or may preferably be connected to the pressure relief tank(s), and the outlet with lower dry matter content may be the digestion tank discharge outlet.

Any combination of digestion tank outlet, i.e. from the top surface, side or bottom, and/or supplemented by an outlet from separator(s) having a lower dry matter content, may be applied in the present invention. However, in order to obtain the largest differentiation between SRT and HRT the outlet via separator(s) may be maximized and the outlet directly from the digestion tank may be minimized.

In one embodiment of the invention, the method or the device further comprises a separator connected to the recirculation loop from the digestion tank(s) for separation of solids, having one outlet with increased dry matter content and one outlet with lower dry mater content, the outlet with increased dry matter content is connected to the pressure relief tank(s), and the outlet with lower dry matter content is the digestion tank discharge outlet. In this embodiment the separator preferably may be a hydrocyclone.

In one embodiment of the invention, the method or the device further comprises a separator for separation of solids connected to a digestion tank discharge outlet; the separator, having one outlet with increased dry matter content and one outlet with lower dry matter content, the outlet with increased dry matter content is connected to an inlet to the thermal hydrolysis reactor(s) or is connected to a biomass feed to the thermal hydrolysis reactor(s); and the outlet with lower dry matter content is a discharge outlet from the process. In this manner the separated part having an increased dry matter content may be returned to the thermal hydrolysis reactor for a second thermal hydrolysis treatment. In this specific embodiment the separator preferably may be selected from a centrifuge, belt thickener, belt press, filter press and a screw press. The device or method may have only discharge outlet(s) via a separator or it may both have discharge outlets via the separator and directly from the digestion tank.

A separator may typically be a cyclone, such as e.g. a hydrocycloen, centrifuge, belt thickener, belt press, filterpress, screw press or any other adequate separation or dewatering machine.

In one embodiment of the invention three reactors in parallel are provided. The number of reactors can be different from this. With the three reactors one can achieve a continuous filing of the reactors.

The device according to the invention may include more than one pressure relief tank(s). By using at least two pressure relief tanks in series it is possible to recover more energy.

According to an embodiment of the invention, the device further may but not necessarily comprise a heat exchanger connected to the digestion tank(s) and the pressure relief tank(s) for condensing a part of the gas phase from the pressure relief tank(s) by using a part of the content of the digestion tank as cooling medium. In case of two stage pressure relief tank solution, the second tank may be equipped with internal cooling circuit instead of recycling of the digestion tank.

In one embodiment of the invention, the device further comprises an extraction component for separation of furfurals from the condensed gas phase.

In another embodiment according to the invention, the heat exchanger is connected to the digestion tank(s) for recycling of the volatile acids in the condensed gas phase.

The features and embodiments described herein in relation to the method of the invention applies mutatis mutandis to the device according to the invention; and vice versa.

DETAILED DESCRIPTION OF THE DRAWINGS

Figure 1:
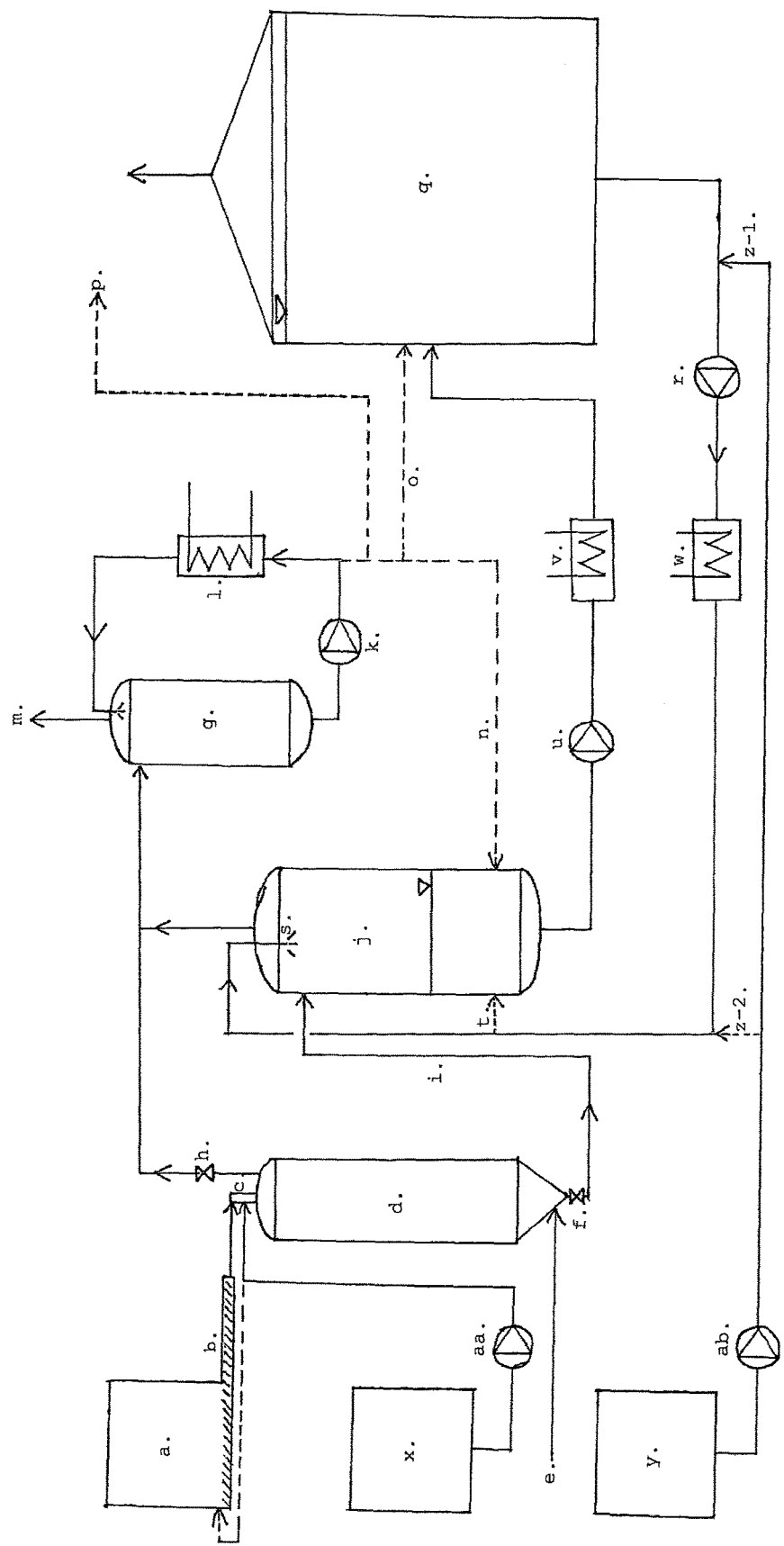
FIG. 1 shows (schematically) an embodiment of the present invention.
Figure 2:
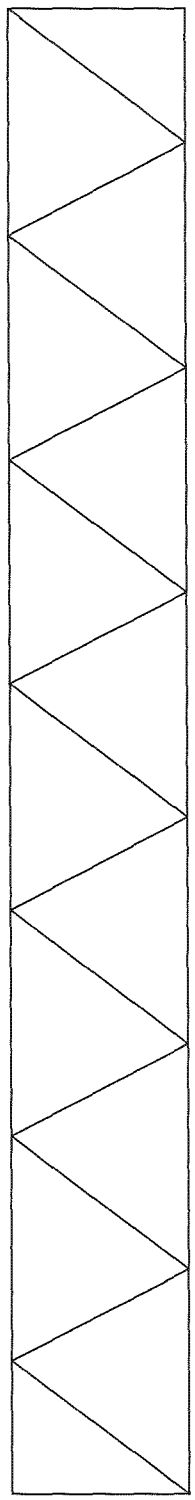
FIG. 2 shows (schematically) a typical embodiment of known prior art methods, involving e.g. the use of a worm-spiral- or helical-conveyers for transporting material with high dry matter content through pipes.

FIG. 1 shows a method and device for pretreating biomass and organic waste fractions with subsequent biological degradation such as anaerobic digestion.

Solid biomass and/or organic waste fraction received, usually in a reception/storage (a) bin is conveyed (b) through a feeding device (c), usually a feed valve or steam assisted feed system, to one or multiple high pressure reactors (d). Steam at high pressure (e) is added into the reactor(s) and by closing inlet and outlet valves (c and f), a sufficient pressure is reached for achieving beneficial hydrolysis of received biomass. When sufficient steam pressure is reached, valves are kept closed until beneficial holding time is elapsed. Depending on the characteristics of the feedstock, there may be beneficial to remove some gases during heating and holding time. If these gases are not emitted, the gases may be led to a condenser system (g) through a release valve (h). At the elapse of the holding time, pressure may be reduced through the release valve (h) prior to opening the discharge valve (f). When the discharge valve is opened, pretreated material is rapidly discharged to the Flashtank (j) through a firmly supported discharge pipe (i). The discharge rate is driven by the pressure difference between the reactor and downstream Flashtank (j). Due to the pressure drop, condensed steam will flash off and is separated from material and water inside the Flashtank (j). Surplus flashsteam released inside the Flashtank (j) is released out of the Flashtank top through a pipe. The flashsteam is preferably led to a condenser (g). The condenser preferably consisting of a quench tower with a circulation pump (k) and a condensate cooler (l), liquefy surplus steam. The condenser may alternatively operate with cold cooling water directly injected into the condenser (g). Non condensables (m) are discharged out of the condenser whereupon odour treatment may be necessary. Condensate is either discharged back to the Flashtank (n), piped (o) to downstream process, or separated from the process possibly for further processing for recovery of chemicals (p). Biological degraded material, for example digestate from downstream anaerobic digester(s) (q) is circulated to the Flashtank with a digester circulation pump (r). Through injection into the Flashtank below liquid level (t), mixing inside the Flashtank is achieved. If condensation inside the Flashtank is preferred, the recycled stream is led to the top of the Flashtank through a nozzle (s) whereupon the Flashtank serves as a quench for condensation of flash steam. Such condensation may not be beneficial due to all production of inhibitors. In such case, the condensation should take place inside a separate condenser (g). The mixture of pretreated material, condensate and recycled biological degraded material such as digestate will be pumped to the downstream process such as anaerobic digester (q) with a feed pump (u). Depending on preferred temperature in downstream process, cooling can take place in a cooler (v or w).

Liquid biomass (x) that benefits from thermal pretreatment can be added to the reactor (d) directly or through the feed system (a or b) for beneficial mixing prior to the reactor. Liquid biomass (y) with less benefit from thermal pretreatment may be directed into the Flashtank directly, or into the digester circulation loop (z-1 or z-2). Adequate pumps (aa and ab) must be selected for transport of liquid biomass into the process.

FIG. 3 shows a further example of a method and device for first pretreating biomass, e.g. organic waste and subsequent biological degradation by fermentation. FIG. 3 is as described for FIG. 1, except there are no condensate cooler (l) and no discharge of condensate (n) back to the flash tank (j), however two possible connections for dilution with water is shown, one via the recirculation loop to the flash tank (af) and one connected to the inlet (c) to the thermal hydrolysis reactor (d). Further shown is a separator or thickener (ac) connected to the recirculation loop between digestion tank (q) and flash tank (j), the separator (ac) having an output (ad). A direct outlet from the digestion tank (q) is shown as (ae).

FIG. 4 shows a further example of a method and device for first pretreating biomass by thermal hydrolysis (d) and wet explosion (j) and subsequently fermenting the intermediate product obtained thereby in a digestion tank (q), wherein part of the content of the digestion tank is transported in a recirculation loop (t) into the pressure relief tank (j). Solid biomass and/or organic waste fraction received, usually in a reception/storage bin (a), is conveyed (b) through a feeding device (c), e.g. a feed valve or steam assisted feed system, to one or multiple high pressure reactors (d). Liquid biomass (x) that benefits from thermal hydrolysis can be added to the reactor (d) directly, or through the feed system (a or b) for beneficial mixing prior to the reactor. Steam at high pressure (e) is added into the reactor(s) (d) and by closing inlet and outlet valves (c and f), a sufficient pressure and temperature is reached for achieving beneficial hydrolysis of received biomass. When sufficient steam pressure is reached, valves are kept closed until beneficial holding time is elapsed. Depending on the characteristics of the feedstock, there may be beneficial to remove some gases through a release valve (h). Pressure may be reduced through the release valve (h). When the discharge valve (f) is opened, pretreated material is rapidly discharged to the pressure relief tank (j) through a discharge pipe (i). The discharge rate is driven by the pressure difference between the reactor and downstream pressure relief tank (j). Due to the pressure drop, condensed steam will flash off and may be released out of the pressure relief tank top through a pipe. Fermented material, for example digestate, from downstream digestion tank(s) (q) is circulated to the pressure relief tank (j) with a digester circulation pump (r), and via a separator or thickener (ac). The separator (ac) having an output (ad) and a further direct outlet from the digestion tank (q) is shown as (ae). Through injection into the pressure relief tank below liquid level (t), mixing inside the pressure relief tank (j) is achieved. If condensation inside the pressure relief tank (j) is preferred, the recycled stream is led to the top of the pressure relief tank (j) through a nozzle (s) hereby serving as a quench for condensation of flash steam. The mixture of pretreated material and recycled biological degraded material such as digestate will be pumped to the downstream process such as digestion tank(s) (q) with a feed pump (u). Depending on preferred temperature in downstream process, cooling can take place in a cooler (v or w). Liquid biomass (y) with less benefit from thermal pretreatment may be directed into the pressure relief tank (j) directly, or into the circulation loop from the digestion tank (z-1 or z-2). Dilution with water may be directed into the process via the recirculation loop (af) to the flash tank (j) or directly (ag) to the inlet (c) to the thermal hydrolysis reactor (d). Adequate pumps (aa and ab) must be selected for transport of liquid biomass into the process. A direct outlet from the digestion tank (q) is shown as (ae).

FIG. 5 shows a further embodiment of the present invention, in which part of the content of the digestion tank (q) is dewatered in separator (ah) and returned as so-called dewatered cake having an increased dry matter (dry solid) content to the feed line (a) for the hydrolysis step thereby mixing it together with the biomass material otherwise feed into the process.

The invention claimed is:

1. A method for treating a biomass material comprising at least the steps of:
    pre-treatment of said biomass material comprising the steps of:
        1) thermal hydrolysis at a temperature above 140° C., followed by
        2) wet explosion resulting in an intermediate product having a dry matter concentration above 25%, a pH below 6 and a temperature above 90° C.;
    subsequent fermentation of said intermediate product in a digestion tank,
    wherein said intermediate product is introduced into said digestion tank by mixing said intermediate product into part of a content of said digestion tank being transported in a recirculation loop emerging from said digestion tank,
    wherein said mixing is performed before the mixture of said intermediate product and said part of the content of said digestion tank enters said digestion tank,
    wherein said part of the content of said digestion tank has a pH in a range of 7-8.5, and
    wherein the pH after said mixing and before the mixture enters said digestion tank is above pH 6.

2. The method according to claim 1, wherein the intermediate product has a temperature above 100° C.

3. The method according to claim 1, wherein the intermediate product has a pH below 5.

4. The method according to claim 1, wherein the method further comprises a wet oxidation, which is performed after the thermal hydrolysis and before the wet explosion.

5. The method according to claim 1, wherein the part of the content of the digestion tank is mixed with the intermediate product in a way that at least 10 parts by volume of the content of the digestion tank is mixed with one part by volume of the intermediate product.

6. The method according to claim 1, wherein a part of a gas phase from the pre-treatment is condensed by using a part of the content of the digestion tank as a cooling medium.

7. The method according to claim 6, wherein furfurals in the gas phase from the pre-treatment are separated by extraction after condensing.

8. The method according to claim 6, wherein volatile acids in the gas phase from the pre-treatment are recycled to the digestion tank after condensing.

9. The method according to claim 1, wherein the biomass material introduced to the method has a dry matter concentration above 50% by weight.

10. The method according to claim 1, wherein the biomass material introduced to the method is chosen from the group consisting of straw, wood, fibres, baits, paper pulp, slurry and household waste.

11. The method according to claim 1, wherein
    the thermal hydrolysis is performed at a temperature above 140'C and maintained for 5-30 minutes followed by,
    wet explosion carried out by reducing a pressure from 5-35 bar to atmospheric pressure.

12. The method according to claim 1, wherein the pH after mixing the intermediate product with recirculated fermentation product from the digestion tank and before the mixture enters said digestion tank is above pH 6.5.

13. The method according to claim 1, wherein the content of the digestion tank and the intermediate product are mixed in a volume ratio range of 3:1-30:1.

14. The method according to claim 1, wherein the part of the content of the digestion tank is mixed with the intermediate product in a way that at least 20 parts by volume of the content of the digestion tank is mixed with one part by volume of the intermediate product.

15. The method according to claim 2, wherein the intermediate product has a pH below 5.

16. The method according to claim 2, wherein the method further comprises a wet oxidation, which is performed after the thermal hydrolysis and before the wet explosion.

17. The method according to claim 3, wherein the method further comprises a wet oxidation, which is performed after the thermal hydrolysis and before the wet explosion.

18. The method according to claim 2, wherein the part of the content of the digestion tank is mixed with the intermediate product in a way that at least 10 parts by volume of the content of the digestion tank is mixed with one part by volume of the intermediate product.

* * * * *